United States Patent [19]

Escher et al.

[11] Patent Number: 5,266,697
[45] Date of Patent: Nov. 30, 1993

[54] PROCESS FOR THE PRODUCTION OF 2-SUBSTITUTED 4,6-DIALKOXYPYRIMIDINES

[75] Inventors: André Escher, Naters; Felix Previdoli, Brig, both of Switzerland

[73] Assignee: Lonza Ltd., Gampel/Valais, Switzerland

[21] Appl. No.: 980,628

[22] Filed: Nov. 23, 1992

[30] Foreign Application Priority Data

Nov. 26, 1991 [CH] Switzerland .......................... 3454/91

[51] Int. Cl.⁵ .................. C07D 239/52; C07D 239/42
[52] U.S. Cl. .................................. 544/320; 544/321; 544/299; 544/319
[58] Field of Search ............... 544/319, 320, 321, 299

[56] References Cited

FOREIGN PATENT DOCUMENTS 024200 2/1981 European Pat. Off. .
249708 12/1987 European Pat. Off. .
64-40470 2/1989 Japan .

OTHER PUBLICATIONS

J. A. Bee and F. L. Rose, J. Chem. Soc., C, (1966), pp. 2031 to 2038.
H. C. Koppel et al., J. Org. Chem., 26, (1961), pp. 792 to 803.

Primary Examiner—John M. Ford
Attorney, Agent, or Firm—Fisher, Christen & Sabol

[57] ABSTRACT

A process for the production of 2-substituted 4,6-dialkoxypyrimidines starting from a cyanimidate of the general formula:

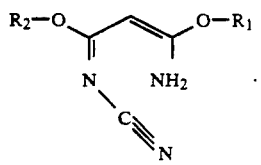

II

The cyanimidate is cyclized with a hydrogen halide to a halopyrimidine derivative of general formula:

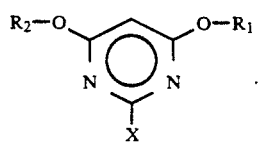

III

The latter is then converted either with a compound of the formula:

M—R₃    IV or with an alkyl amine of the general formula:

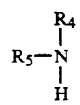

V into the end product of the general formula:

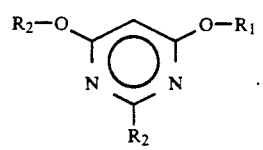

I

15 Claims, No Drawings

PROCESS FOR THE PRODUCTION OF 2-SUBSTITUTED 4,6-DIALKOXYPYRIMIDINES

BACKGROUND OF THE INVENTION

Field Of The Invention

The invention relates to a process for the production of 2-substituted 4,6-dialkoxypyrimidines of the general formula:

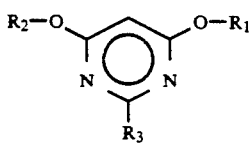   I wherein in $R_1$ and $R_2$ are the same or different and each is a $C_1$–$C_4$ alkyl group and $R_3$ is an $R_4$—O—, $R_4$—S— or

 group, wherein $R_4$ is a $C_1$–$C_4$ alkyl group and $R_5$ is a hydrogen atom, a $C_1$–$C_4$ alkyl group or a phenyl group, starting from a cyanimidate.

Background Art

The 2-substituted 4,6-dialkoxypyrimidines of formula I, especially 4,6-dimethoxy-2-(methylthio)pyrimidine, are important intermediate products for the production of herbicides (European Published Patent Application No. 249,708).

A known embodiment for the production of a halopyrimidine derivative is described in J. A. Bee and F. L. Rose. J.Chem.Soc., C, (1966), pp. 2031–2038. In the process the halopyrimidine derivative 2-chloro-4,6-dimethoxy-pyrimidine is synthesized by diazotization of 2-amino-4,6-dimethoxy-pyrimidine with sodium nitrite and subsequent hydrolysis with concentrated hydrochloric acid.

A major drawback of the process lies in that 2-chloro-4,6-dimethoxypyrimidine is obtained in a very poor yield.

A known embodiment for the production of 4,6-dialkoxy-2-alkylthiopyrimidines, starting from 4,6-dihydroxy-pyrimidines and organic sulfonic acids, is described in Japanese Laid-Open Patent Application No. 01-040470. The process also has the drawback that the 4,6-dialkoxy-2-alkylthiopyrimidines are obtained in very poor yields.

In addition, 4,6-dimethoxy-2-(methylthio)-pyrimidine can be produced by substitution of the halogen atoms in 4,6-dichloro-2-methylthiopyrimidine by alkali methylate. Here first the feedstock 4,6-dichloro-2-methylthiopyrimidine is produced by chlorination of 2-methylthiobarbituric acid with phosphoric oxide trichloride [*J. Org. Chem.*, 26, (1961), pp. 792–803]. Then the 4,6-dichloro-2-methylthiopyrimidine can be converted according to methods usual to one skilled in the art by alkali methylate into 4,6-dimethoxy-2-(methylthio)-pyrimidine. The process has the drawback that in this way large amounts of phosphate accumulate for disposal as waste product.

BROAD DESCRIPTION OF THE INVENTION

The main objective of the invention is to eliminate such drawbacks and to provide a simple and ecological process with good yields for the production of 2-substituted 4,6-dialkoxypyrimidines. Other objectives and advantages of the invention are set out herein or are obvious herefrom to one skilled in the art.

The objectives and advantages of the invention are achieved by the processes and compounds of the invention.

The invention involves a process for the production of 2-substituted 4,6-dialkoxypyrimidines of the general formula:

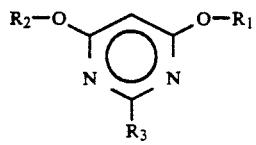   I wherein $R_1$ and $R_2$ are the same or different and each is a $C_1$–$C_4$ alkyl group and $R_3$ is an $R_4$—O—, $R_4$—S— or

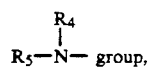 group, wherein $R_4$ is a $C_1$–$C_4$ alkyl group and $R_5$ is a hydrogen atom, a $C_1$–$C_4$ alkyl group or a phenyl group. In the first step, a cyanimidate of the general formula:

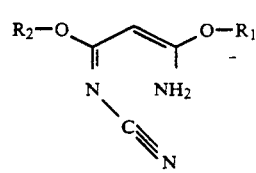   II wherein $R_1$ and $R_2$ have the above-mentioned meanings, is cyclized with a hydrogen halide to a halopyrimidine derivative of the general formula:

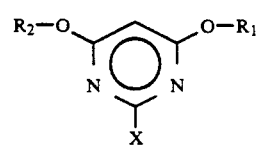   III wherein $R_1$ and $R_2$ have the above-mentioned meanings, and X is a halogen atom. The latter is then converted in the second step either with a compound of the general formula:

M—$R_3$   IV wherein $R_3$ is the above-mentioned $R_4$—O— or $R_4$—S— group and M is an alkali metal atom, or with an alkyl amine of the general formula:

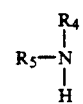   V wherein $R_4$ and $R_5$ have the above-mentioned meanings, into the end product according to the formula I.

Preferably, in the first step, 3-amino-3-methoxy-N-cyano-2-propenimidate, wherein $R_1$ and $R_2$ each is a methyl group, is used as the imidate. Preferably, in the first step, hydrogen chloride is used as the hydrogen halide. Preferably the reaction is performed in the first step at a temperature of $-30°$ to $+30°$ C. Preferably, in the second step, an alkali metal thiolate or an alkali metal methanolate is used as the compound of the general formula IV. Preferably, in the second step, an alkyl amine of the general formula V is used wherein $R_4$ is a butyl group and $R_5$ is a hydrogen atom. Preferably the reaction in the second step is performed at a temperature of $-10°$ to $100°$ C. Preferably the reaction is performed without isolation of the halopyrimidine derivative according to the formula III.

The invention also involves 2-N-alkylamino-4,6-dialkoxypyrimidines of the general formula:

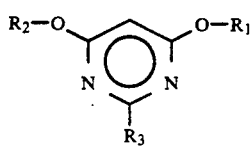   I wherein $R_1$ and $R_2$ are the same or different and each is a $C_1$–$C_4$ alkyl group, $R_3$ is an

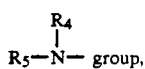 group, wherein $R_4$ is a $C_1$–$C_4$ alkyl group and $R_5$ is a hydrogen atom or a $C_1$–$C_4$ alkyl group. Preferably the compound is 2-N-butylamino-4,6-dimethoxypyrimidine.

The invention further involves a process for the production of halopyrimidine derivatives of the general formula:

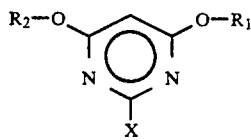   III wherein $R_1$ and $R_2$ have the above-mentioned meanings, wherein a cyanimidate of the general formula:

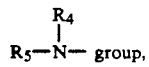 group, wherein $R_1$ and $R_2$ have the above-mentioned meanings, is reacted with a hydrogen halide.

DETAILED DESCRIPTION OF THE INVENTION

According to the invention the process is performed so that in the first step a cyanimidate of the general formula:

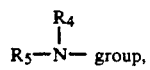 group, wherein $R_1$ and $R_2$ have the above-mentioned meanings, is cyclized with a hydrogen halide to a halopyrimidine derivative of the general formula:

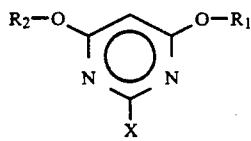   III wherein $R_1$ and $R_2$ have the above-mentioned meanings and X is a halogen atom. The halopyrimidine derivative is then converted in the second step either with a compound of the general formula:

$M-R_3$   IV wherein $R_3$ is the above-mentioned $R_4$—O— or $R_4$—S— group and M is an alkali metal atom, or with an alkyl amine of general formula:

   V wherein $R_4$ and $R_5$ have the above-mentioned meaning, into the end product according to the formula I.

The first step is suitably performed with imidates of the general formula:

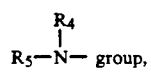 group, wherein $R_1$ and $R_2$ each is a methyl group or an ethyl group. Preferably 3-amino-3-methoxy-N-cyano-2-propenimidate is used as the imidate of the formula II, wherein $R_1$ and $R_2$ each is a methyl group. 3-Amino-3-methoxy-N-cyano-2-propenimidate can, for example, be produced in a simple way according to European Published Patent Application No. 024200.

As the hydrogen halide, hydrochloric acid, hydrobromic acid or hydroiodic acid can be used in the first step; preferably hydrochloric acid is used. The hydrogen halide can be used in an amount of 2 to 4 mol per mol of cyanimidate of the formula II. Preferably the hydrogen halide is introduced as a gas in the reaction mixture up to saturation. The temperatures during the reaction in the first step are suitably between $-30°$ and $+30°$ C., preferably between $-20°$ and $+10°$ C. For the reaction in the first step, an inert inorganic solvent, such as, tetrahydrofuran, toluene, acetonitrile, methylene chloride or low-boiling alcohols can be used as the solvent. Preferably toluene is used as the solvent.

Then, after a usual reaction time of 1 to 5 hours, the halopyrimidine derivative of formula III can be worked up according to a method usual to one skilled in the art, or used directly, without isolation, for the second step.

For the reaction in the second step the suitable representatives of the compounds of the general formula:

$M-R_3$   IV are those wherein $R_3$ is methanolate or ethanolate, preferably methanolate, or thiolate and M is an alkali metal atom, as described. The preferred representatives of the compounds of the formula IV are: sodium methanolate, potassium methanolate, sodium thiolate and potassium thiolate.

For the reaction in the second step, also usefully suitable as representatives are the alkyl amines of the general formula:

   V wherein $R_4$ is a $C_1-C_4$ alkyl group and $R_5$ is a $C_1-C_4$ alkyl group or a hydrogen atom. Preferably butyl amine is used as the alkyl amine, wherein $R_4$ is a butyl group and $R_5$ is a hydrogen atom.

The compounds of the general formula IV or V can be used in an amount of 1 to 3 mol, preferably of 1 to 2 mol, per mol of halopyrimidine derivative of the formula III.

The temperatures in the reaction in the second step are suitably between $-10°$ and $100°$ C., preferably between $40°$ and $80°$ C. As the solvent for the reaction in the second step, the same solvents as those in the first step can be used.

Then, after a usual reaction time of 1 to 50 hours, the end product according to the formula I is worked up according to methods usual to one skilled in the art.

Preferably the entire reaction is performed without isolation of the halopyrimidine derivative according to the formula III.

The 2-N-alkylamino-4,6-dialkoxypyrimidines of the general formula:

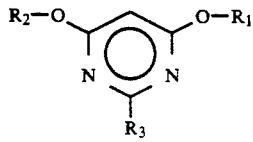   I wherein $R_3$ is an

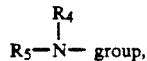  group, wherein $R_4$ is a $C_1-C_4$ alkyl group and $R_5$ is a hydrogen atom or a $C_1-C_4$ alkyl group, are new and, thus, also are a part of the invention. As the preferred representative of these new compounds, 2-N-butylamino-4,6-dimethoxypyrimidine is mentioned and produced.

EXAMPLE 1

Process for the production of 2-chloro-4,6-dimethoxyorimidine (a) Tetrahydrofuran as the solvent 4.7 g of 3-amino-3-methoxy-N-cyano-2-propenimidate was suspended in 60 ml of tetrahydrofuran and cooled to $-20°$ C. Hydrochloric acid gas was introduced up to saturation and the temperature held in the range of $-10°$ to $-20°$ C. Over a period of 3 hours, in intervals of 30 minutes, so much hydrochloric acid gas each was introduced that the solution was again saturated. The tetrahydrofuran was completely distilled; after addition of 50 ml of water, extraction with methylene chloride was performed three times; and, after drying on sodium sulfate, the organic phase was completely concentrated by evaporation. 4.0 g of crystalline white product was obtained corresponding to a yield of 71.1 percent relative to the propenimidate used. The melting point of the product was 99 to 100° C. The content was 94 percent (GD).

The product was able to be recrystallized as follows:

The above crude pyrimidine was heated in 25 ml of isopropanol to $70°$ C. After addition of water until the onset of clouding it was cooled to $10°$ C and filtered off. After drying 3.5 g of pure product was obtained which corresponded to a yield of 66.2 percent relative to the propenimidate. The recrystallized product had a melting point of $102°$. The content was $>99$ percent (GC). Elementary analysis for $C_6H_7ClN_2O_2$: Found: C=40.8% H=4.0% N=16.0% Calculated: C=41.3% H=4.0% N=16.1%

Other data for the recrystallized product was:

$^1$H-NMR (CDCl$_3$, 300 MHz) $\delta$ in ppm: 5.97 (s, 1H); 3.95 (s, 6H). (b) Toluene as the solvent A suspension of 2.4 g of 3-amino-3-methoxy-N-cyano-2-propenimidate in 20 ml of toluene was saturated at $0°$ with hydrochloric acid gas. The suspension was stirred for 2 hours, and the HCl stream was maintained, so that the reaction mixture always remained saturated. 20 ml of water was added, the phases separated and the aqueous phase was extracted twice more with 10 ml of toluene. The combined organic phases were completely concentrated by evaporation and dried in a high vacuum. 2.1 g of white crystalline product with a GC-content of 95 percent was obtained, which corresponded to a yield of 73.9 percent relative to propenimidate. The melting point of the product was $100°$ C.

EXAMPLE 2

Process for the production of 4,6-dimethoxy-2-methylthiopyrimidine

2-Chloro-4,6-dimethoxypyrimidine was produced as in Example 2. The organic phases obtained after extraction were instilled at room temperature in a solution of 1.5 molar equivalent of sodium thiolate in 5 ml of methanol. To complete the reaction, it was heated after 2 hours to $50°$ C. and held at this temperature for 2 hours. After extraction with 20 ml of water, concentration by evaporation and drying in a high vacuum, 1.8 g of white crystalline product was obtained, which corresponded to a yield of 60 percent relative to the propenimidate. The product had a melting point of $49°$ to $50°$ C.

A product with a melting point of $54°$ to $56°$ C. was obtained by recrystallization from isopropanol/water. Other data concerning the recrystallized product was:

$^1$H-NMR (CDCl$_3$, 300 MHz) $\delta$ in ppm: 5.72 (s, 1H); 3.95 (s, 6H); 2.55 (s, 3H).

EXAMPLE 3

Process for the production of 2-N-butylamino-4,6-dimethoxypyrimidine

A solution of 1.9 g of 2-chloro-4,6-dimethoxypyrimidine in 30 ml of toluene [from Example 1(b)] was mixed with 2.7 g of butylamine and 3.3 g of triethylamine and maintained during 50 hours at $80°$ C. After cooling, it was extracted twice with 30 ml of water and then the organic phase was completely concentrated by evaporation. The light yellow oil was distilled at $140°$ C./1 mbar. 2.1 g of a colorless oil was obtained corresponding to a yield of 66 percent relative to the propenimidate. The content was 98 percent (GC). Other data for the product was:

$^1$H-NMR (CDCl$_3$, 300 MHz) δ in ppm: 5.4 (s, 1H); 4.95 (b, 1H); 3.85 (s, 6H); 3.4 (q, 2H); 1.55 (m, 2H); 1.4 (m, 2H); 0.95 (t, 3H).

Elementary analysis for C$_{10}$H$_{17}$N$_3$O$_2$: Found: C=56.9% H=8.5% N=19.6% Calculated: C=56.9% H=8.1% N=19.9%

EXAMPLE 4

Process for the production of 2,4,6-trimethoxyoyrimidine 1.3 g of 2-chloro-4,6-dimethoxypyrimidine from Example 1(a) (content 94 percent) was dissolved in 9 ml of methanol. After addition of 2.5 g of sodium methanolate solution (30 percent in methanol), it was stirred for two hours at 55° C. After cooling, the precipitated sodium chloride was filtered off and the filtrate mixed with 15 ml of water. During standing in an ice bath the product crystallized as fine white needles; that were filtered off and dried at room temperature in a vacuum. 1.02 g of pure product was obtained corresponding to a yield of 86 percent. The product had a melting point of 55° C. Other data for the product was:

$^1$H-NMR (CDCl$_3$, 300 MHz) δ in ppm: 5.7 (s, 1H); 4.0 (s, 3H); 3.95 (s, 6H).

What is claimed is:

1. A process for the production of a 2-substituted 4,6-dialkoxypyrimidines of formula:

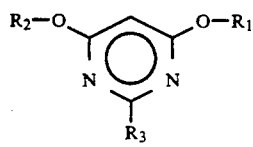   I wherein R$_1$ and R$_2$ are the same or different and each is a C$_1$-C$_4$ alkyl group and R$_3$ is an R$_4$—O—, R$_4$—S—

wherein R$_4$ is a C$_1$-C$_4$ alkyl group and R$_5$ is an hydrogen atom, a C$_1$-C$_4$ alkyl group or a phenyl group, characterized in that, in a first step, a cyanimidate of formula:

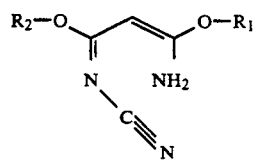   II wherein R$_1$ and R$_2$ have the above-mentioned meanings, is cyclized with a hydrogen halide to a halopyrimidine derivative of formula:

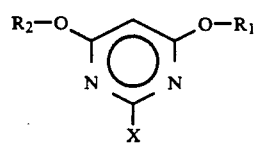   III wherein R$_1$ and R$_2$ have the above-mentioned meanings and X is a halogen atom, and, in the second step, the latter is then converted either with a compound of formula:

M—P$_3$   IV wherein R$_3$ is the above-mentioned R$_4$—O— or R$_4$—S— group and M is an alkali metal atom or with an alkyl amine of formula:

   V wherein R$_4$ and R$_5$ have the above-mentioned meanings, into the end product according to formula I.

2. The process according to claim 1, wherein, in the first step, 3-amino-3-methoxy-N-cyano-2-propenimidate, wherein R$_1$ and R$_2$ each is a methyl group, is used as the imidate.

3. The process according to claim 2 wherein, in the first step, hydrogen chloride is used as the hydrogen halide.

4. The process according to claim 3 wherein the reaction is performed in the first step at a temperature of −30 to +30° C.

5. The process according to claim 1 wherein, in the second step, an alkali metal thiolate or an alkali metal methanolate is used as the compound of formula IV.

6. The process according to claim 1 wherein, in the second step, an alkyl amine of formula V is used wherein R$_4$ is a butyl group and R$_5$ means a hydrogen atom.

7. The process according to claim 6 wherein the reaction in the second step is performed at a temperature of −10° to 100° C.

8. The process according to claim 4 wherein the reaction is performed without isolation of the halopyrimidine derivative according to formula III.

9. The process according to claim 1 wherein, in the first step, hydrogen chloride is used as the hydrogen halide.

10. The process according to claim 1 wherein the reaction is performed in the first step at a temperature of −30° to +30° C.

11. The process according to claim 1 wherein the reaction in the second step is performed at a temperature of −10° to 100° C.

12. The process according to claim 1 wherein the reaction is performed without isolation of the halopyrimidine derivative according to formula III.

13. A 2-N-alkylamino-4,6-dialkoxypyrimidine of formula:

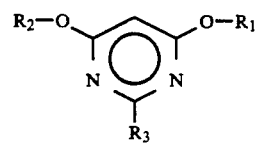   I wherein R$_1$ and R$_2$ are the same or different and each is a C$_1$-C$_4$ alkyl group, R$_3$ is an

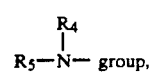 group, wherein $R_4$ is a $C_1$–$C_4$ alkyl group and $R_5$ is a hydrogen atom or a $C_1$–$C_4$ alkyl group.

14. 2-N-butylamino-4,6-dimethoxypyrimidine.

15. A process for the production of a halopyrimidine derivative of formula:

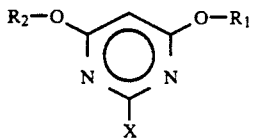
III wherein $R_1$ and $R_2$ are the same or different and each is a $C_1$–$C_4$ alkyl group, wherein X is a halogen atom comprising reacting a cyanimidate of formula:

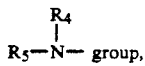
group, wherein $R_1$ and $R_2$ have the above-mentioned meanings, with a hydrogen halide.

* * * * *

UNITED STATES PATENT AND TRADEMARK OFFICE
CERTIFICATE OF CORRECTION

PATENT NO. : 5,266,697
DATED : Nov. 30, 1993
INVENTOR(S) : Escher et al.

It is certified that error appears in the above-identified patent and that said Letters Patent is hereby corrected as shown below:

Column 10

Claim 15, delete the second formula "$R_5 - \overset{R_4}{\underset{|}{N}} - \text{group},$"

and insert therefor -- 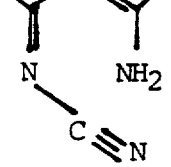 II --

Signed and Sealed this

Fifth Day of December, 1995

*Attest:*

BRUCE LEHMAN

*Attesting Officer*   Commissioner of Patents and Trademarks